(12) United States Patent
Barak

(10) Patent No.: US 9,713,434 B2
(45) Date of Patent: Jul. 25, 2017

(54) MICROWAVE CONTACTLESS HEART RATE SENSOR

(71) Applicant: SENSIFREE LTD., Kfar Sava (IL)

(72) Inventor: Ilan Saul Barak, Kfar Saba (IL)

(73) Assignee: SENSIFREE LTD., Petach Tikva (IL)

( * ) Notice: Subject to any disclaimer, the term of this patent is extended or adjusted under 35 U.S.C. 154(b) by 195 days.

(21) Appl. No.: 14/377,845

(22) PCT Filed: Feb. 7, 2013

(86) PCT No.: PCT/IL2013/050113
§ 371 (c)(1),
(2) Date: Aug. 8, 2014

(87) PCT Pub. No.: WO2013/118121
PCT Pub. Date: Aug. 15, 2013

(65) Prior Publication Data
US 2015/0018676 A1    Jan. 15, 2015

Related U.S. Application Data

(60) Provisional application No. 61/597,734, filed on Feb. 11, 2012.

(51) Int. Cl.
*A61B 5/05*    (2006.01)
*A61B 5/024*   (2006.01)
(Continued)

(52) U.S. Cl.
CPC ............ *A61B 5/0507* (2013.01); *A61B 5/026* (2013.01); *A61B 5/02444* (2013.01);
(Continued)

(58) Field of Classification Search
CPC ... A61B 5/02444; A61B 5/026; A61B 5/0507; A61B 5/681
See application file for complete search history.

(56) References Cited

U.S. PATENT DOCUMENTS

| 4,085,740 A | 4/1978 | Allen, Jr. |
| 4,958,638 A | 9/1990 | Sharpe et al. |

(Continued)

FOREIGN PATENT DOCUMENTS

| EP | 2290392 A1 | 3/2011 |
| JP | 2005102959 | 4/2005 |

(Continued)

OTHER PUBLICATIONS

Beilleau, Nicholas et al., "A 1.3V 26mW 3.2GS/s Undersampled LC bandpass Σ Δ ADC for a SDR ISM-band Receiver in 130nm CMOS", IEEE Radio Frequency Integrated Circuits Symposium, (RFIC '09), pp. 383-386, Jun. 1, 2009.

(Continued)

Primary Examiner — Baisakhi Roy
(74) Attorney, Agent, or Firm — Neifeld IP Law, PC

(57) ABSTRACT

A heart-rate sensor for detecting artery blood-flow volume per unit length change in a human or animal subject, which comprises an antenna for sensing the instantaneous volume of blood in the artery of the subject, to be measured; a RADAR unit for transmitting microwave signals into a subject's body part or limb representing tissue targets. The output of the RADAR unit includes a superposition of signals each of which corresponding to a different tissue target with amplitudes that relate to the target's reflection strength; a sampling circuitry for converting reflected signals to digital; a window function circuitry for suppressing unwanted spectral sidebands originating from the subsequent processor operating on time truncated data; an FFT processor following the window function circuitry, for splitting the superposition according to its relative frequency into a multiplicity of bins, each of which with an amplitude that represents the reflection magnitude of a target at a specific distance from the antenna; a signal processor for filtering out (Continued)

the effect of the sensor movement with respect to the subject body part, or the movement of the body part, and for generating a signal, the amplitude of which is proportional to the artery varying dilatation representing the heart-rate; a heart-rate estimator for measuring the frequency of the artery dilatation variations and for canceling the interference of the amplitude of any signal that does not originate from the artery; a battery for powering the sensor.

54 Claims, 7 Drawing Sheets

(51) Int. Cl.
    *A61B 5/00*          (2006.01)
    *A61B 5/026*       (2006.01)
    *G01S 13/58*       (2006.01)
    *G01S 13/88*       (2006.01)

(52) U.S. Cl.
    CPC ............ *A61B 5/681* (2013.01); *G01S 13/583* (2013.01); *G01S 13/88* (2013.01)

(56) References Cited

U.S. PATENT DOCUMENTS

| | | | | |
|---|---|---|---|---|
| 5,309,907 A * | 5/1994 | Fang | .................... | A61B 5/1455 |
| | | | | 600/342 |
| 5,361,070 A * | 11/1994 | McEwan | .............. | A61B 5/0507 |
| | | | | 342/21 |
| 5,432,482 A * | 7/1995 | Bailey | .................... | H03B 9/147 |
| | | | | 331/107 P |
| 5,807,267 A | 9/1998 | Bryars et al. | | |
| 5,983,127 A * | 11/1999 | dePinto | .............. | A61B 5/04017 |
| | | | | 128/901 |
| 6,026,125 A * | 2/2000 | Larrick, Jr. | ............. | H04L 27/04 |
| | | | | 375/295 |
| 6,028,563 A | 2/2000 | Higgins | | |
| 7,893,886 B2 | 2/2011 | Schadler | | |
| 2002/0151805 A1* | 10/2002 | Sugo | .................. | A61B 5/02125 |
| | | | | 600/504 |
| 2006/0094937 A1* | 5/2006 | Immoreev | .......... | A61B 5/02438 |
| | | | | 600/301 |
| 2007/0219059 A1* | 9/2007 | Schwartz | ............. | A61B 5/0205 |
| | | | | 482/8 |
| 2008/0082009 A1* | 4/2008 | Baker | .................. | A61B 5/0205 |
| | | | | 600/500 |
| 2009/0203972 A1 | 8/2009 | Heneghan | | |
| 2010/0004709 A1* | 1/2010 | Mische | .................. | A61H 23/02 |
| | | | | 607/3 |
| 2010/0027737 A1 | 2/2010 | Mostov | | |
| 2010/0179438 A1 | 7/2010 | Heneghan et al. | | |
| 2010/0198083 A1 | 8/2010 | Lin et al. | | |
| 2011/0130800 A1* | 6/2011 | Weinstein | .............. | A61B 8/085 |
| | | | | 607/17 |
| 2011/0304497 A1 | 12/2011 | Molyneux et al. | | |
| 2012/0109236 A1* | 5/2012 | Jacobson | ................ | A61N 1/368 |
| | | | | 607/4 |
| 2012/0296221 A1* | 11/2012 | Morren | .................. | A61B 5/113 |
| | | | | 600/484 |
| 2013/0245436 A1* | 9/2013 | Tupin, Jr. | ............. | A61B 5/0444 |
| | | | | 600/430 |
| 2014/0358140 A1* | 12/2014 | Emmons | ............ | A61B 18/1815 |
| | | | | 606/33 |

FOREIGN PATENT DOCUMENTS

| | | |
|---|---|---|
| JP | 2005102959 A | 4/2005 |
| WO | 98/16846 A1 | 4/1998 |
| WO | 00/75687 A1 | 12/2000 |
| WO | WO 0075687 | 12/2000 |
| WO | 2009/067627 A1 | 5/2009 |

OTHER PUBLICATIONS

Mitomo, Toshiya, et al., "A 77 GHz 90 nm CMOS Transceiver for FMCW Radar Applications", IEEE Journal of Solid-State Circuits, vol. 45, No. 4, pp. 928-931, Apr. 2010.
Epson Enters Healthcare Business with Wristwatch-Type Pulse Monitor, Internet site at http://global.epson.com/innovation/technology_articles/201206_2.html, 2 pages, Jun. 29, 2012.
Lin, James C. et al., Microwave Apexcardiography, IEEE Transactions on Microwave Theory and Techniques, vol. Mtt-27, No. 6, pp. 618-620, Jun. 1979.
Tu, Yifeng, "Multiple Reference Active Noise Control", Thesis submitted to Virginia Polytechnic Institute and State University, Mar. 1997.
International Search Report and Written Opinion, mailed Jun. 18, 2013, for PCT/IL2013/050113, filed Feb. 7, 2013.
Sep. 28, 2015, Extended European Search Report for 13746312.1 issued Sep. 28, 2015.
Oct. 15, 2015, Communication pursuant to Rules 70(2) and 70a(2) EPC for application 13746312.1 issued Oct. 15, 2015.
Apr. 1, 2010, Mitomo, T. et al.,"A 77 Ghz 90 nm CMOS Transceiver for FMCW Radar Applications", IEEE Journal of Solid-State Circuits, IEEE Service Center Piscataway, NJ , vol. 45, No. 4, Apr. 1, 2010.

\* cited by examiner

MICROWAVE CONTACTLESS HEART RATE SENSOR

RELATED APPLICATIONS

The present application is a 371 National Stage Application of PCT application no. PCT/IL2013/050113, having an international filing date of Feb. 7, 2013, claiming priority to and benefit of U.S. provisional patent application No. 61/597,734, filed Feb. 11, 2012; both disclosures of which are herein incorporated by reference in their entireties

FIELD OF THE INVENTION

The present invention relates to the field of heart rate sensors. More particularly, the present invention relates to a contactless heart-rate sensor for continuously measuring of heart pulse rate of a human subject or an animal, by utilizing a low power compact microwave sensor.

BACKGROUND OF THE INVENTION

Conventional heart-rate sensors are embedded in monitors and are commonly used in training and sports. There are two common types of heart-rate sensors:

The first type: is a monitor comprising a chest strap sensor and a receiver integrated into a wristwatch. The strap receives ECG signals from the heart and transmits them to the receiver. An example for this type is RS400 Heart Rate Monitor (manufactured by Polar). The chest belt receives ECG signals from the objects body chest via two electrical contacts, and transmits them to the receiver in the wristwatch.

The chest strap associated with this type is inconvenient to wear. Also, in some individuals, the ECG signal reception is too week, due to the varying body surface resistance. This may result in intermittent pulse rate measurements. This monitor type is the only practical solution currently available for continuous heart rate measurement during exercise.

The second type: is a beltless heart rate monitor where an ECG sensor is integrated in a wristwatch. The ECG signals are conducted to the measurement device inside the watch via the two subject's arms. It requires the user to close an electrical circuit by touching the watch with his other hand. An example of this product is the PM18 by Beurer GmbH. However, for continuous pulse rate readout during training, it is impractical to use the beltless solution, as it requires the continuous connection of both hands.

Another type of heart-rate monitor available on the market is ring-shaped, like the Multifunction Digital Ring by Lifespan. This monitor is worn on the finger, utilizing a sensor that measures the blood pulsating in the finger, using infrared imaging. However, this measurement is not sufficiently accurate, especially while in training.

U.S. Pat. No. 4,085,740 discloses heart-rate measurement using microwave sensors. Also, James C. Lin, in his paper titled "Microwave Apexcardiography" in Transactions On Microwave Theory And Techniques, Vol. Mtt-27, No. 6, June 1979 teaches a measurement method of the heart rate, directly from the heart movement. Lin utilized a quadrature homodyne detector to detect the amplitude and phase of the reflected signal from the heart.

U.S. Pat. No. 4,958,638 teaches a method to measure the heart-rate and respiratory rate by directly measuring the heart and lungs movements. This method is able to distinguish between movements of the two. This patent describes a frequency modulated radar, which can be interpreted as FMCW as suggested by US 2010/0179438. However, both patents do not deal with the problem of separating the heart pulse rate measurement from other body organ movements. Such movements frequency, in the case of sport training, fall within the normal heart rate frequency range and are not easy to filter out.

Attempts have been made to filter this interference, for example in U.S. Pat. No. 5,807,267 that suggests using an additional accelerometer to measure the body movement frequency and cancel it, using an FFT (Fast Fourier Transform) technique. FFT for this application implies a long measurement time for reasonable accuracy, which cannot be tolerated in this type of application. Another example of this technique is described in a promotional activity by Epson describing a prototype E200 pulse watch, for example as described in their internet site at http://global.epson.com/innovation/technology_articles/201206_2.html.

All the sensors described above have not provided a satisfactory solution to the problem of the problem of separating the heart pulse rate measurement from other body organ movements and are not sufficiently accurate.

It is therefore an object of the present invention to provide a wireless heart-rate sensor that can separate the heart pulse rate measurement from other body organ movements.

It is another object of the present invention to provide a wireless heart-rate sensor that is accurate, especially for measurements that are made while training.

It is a further object of this invention to facilitate heart rate measurements from a body part which is covered by apparel or by natural fur.

Other objects and advantages of the invention will become apparent as the description proceeds.

SUMMARY OF THE INVENTION

The present invention is directed to a heart-rate sensor for detecting artery blood-flow volume per unit length change in a human or animal subject, which comprises:
  a) an antenna for sensing the instantaneous volume of blood in the artery of the subject, to be measured;
  b) a RADAR unit (e.g., a Modulated Continuous Wave (FMCW) radar) for transmitting, via the antenna, microwave signals into a subject's body part or limb representing tissue targets, the output of the RADAR unit including a superposition of signals, each of which corresponding to a different tissue target, where their amplitudes relate to the target's reflection strength;
  c) a sampling circuitry for converting reflected signals to processable digital representation, preferably at a sampling rate of 10 Hz;
  d) a window function circuitry (e.g., a Kaiser window with $\beta=0.5$, a Tukey Window or a window used in connection with Digital Fourier Transforms), for suppressing unwanted spectral sidebands originating from the subsequent processor operating on time truncated data;
  e) a function processor (such as an FFT function) following the window function circuitry, for splitting the superposition according to its relative frequency into a multiplicity of bins, each of which having an amplitude that represents the reflection magnitude of a target at a specific distance from the antenna;
  f) a signal processor for filtering out the effect of the sensor movement with respect to the subject body part, or the movement of the body part, and for generating a signal, the amplitude of which is proportional to the artery varying dilatation representing the heart-rate; and g) a heart-rate estimator for measuring the frequency of the artery dilatation variations and for canceling the interference of the amplitude of any signal that does not originate from the artery;

h) a power source (e.g., a battery such as a coin type battery) for powering the sensor.

The microwave signal may have a bandwidth of at least 3 GHz.

The RADAR unit may be a Stepped Frequency RADAR or a pulsed RADAR, or may be adapted to use FMCW with a sweep time of 10 μsec and the sampling frequency of the ADC is 3.2 MHz. The FMCW RADAR unit may use triangle wave modulation, multirate ramp, triangular wave modulation or wideband sine-wave modulation.

The interference may be eliminated using Multiple Reference ANC, Recursive Least Squares (RLS), Least Mean Square (LMS), Filtered-X LMS (FxLMS) or FuLMS.

Preferably, the heart-rate sensor may be integrated into a wristwatch.

The heart-rate sensor may include a voltage controlled oscillator (e.g., a variable frequency ring oscillator, fabricated using standard CMOS or BiCMOS technologies) modulated by a ramp signal spanning the full signal bandwidth from 3.1 to 10.6 GHz with a typical sweep time of 10 μs. The VCO output may be coupled to the antenna and to the LO input of a mixer that mixes with the VCO signal to produce an IF signal which is filtered by a Low Pass Filter (LPF) and amplified by an IF amplifier, before being sampled by an Analog to Digital Converter (ADC).

The frequency variation of the oscillator may be in discrete steps.

The antenna may be a dual planar cross-bow dipole antenna which comprises two orthogonal broadband dipoles, a single arm spiral antenna, a single broadband dipole antenna or a slot antenna.

The frequency analysis for splitting the superposition may be performed by using DFT, a chirp-Z transform, or an analog filter bank.

The RADAR unit may operate at a duty cycle below 1%.

The FMCW chirp width may be at least 5 GHz.

The heart-rate sensor may include circuitry for cancellation of interference caused by a movement of the sensor, by using signals from a plurality of time bins.

The interference cancellation may be based on weighted ratios (the ratio between the amplitude of the signal reflected from the artery, to the amplitude of the signal reflected from the skin) of polynomials of multiplicity of range gate bins amplitudes; on adaptive noise cancellation whose input signals are a plurality of these range gate bins amplitudes or on adaptive noise cancellation, where additional one or more inputs are taken from an acceleration sensitive device.

Preferably, the oscillator bandwidth is more than 5 GHz.

The heart-rate sensor may comprise two orthogonal antennas, one for transmitting and one for receiving.

The heart-rate sensor may further include a radio transmitter to relay heart rate data to a remote receiver or terminal and a wrist strap enabling wearing on wrist.

The heart-rate sensor may be embedded in a shoe.

The present inventor is also directed to a method for measuring the heart-rate in a subject, according to which the instantaneous volume of blood in the artery of the subject is sensed by an antenna and microwave signals are transmitted by a RADAR unit, via the antenna, into a subject's limb representing tissue targets. The output of the RADAR unit includes a superposition of signals, each of which corresponding to a different tissue target, where their amplitudes relate to the target's reflection strength. Reflected signals are converted to processable digital representation by a sampling circuitry and unwanted spectral sidebands originating from the subsequent processor operating on time truncated data are suppressed by a window function. The superposition is split by using an FFT function, according to its relative frequency into a multiplicity of bins, each of which having an amplitude that represents the reflection magnitude of a target at a specific distance from the antenna. Then the effect of the sensor movement with respect to the subject body part is filtered out and a signal, the amplitude of which is proportional to the artery varying dilatation representing the heart-rate is generated. The frequency of the artery dilatation variations is measured and the interference of the amplitude of any signal that does not originate from the artery is canceled.

DETAILED DESCRIPTION OF PREFERRED EMBODIMENTS

The sensor proposed by the present invention measures the variations in the blood volume flowing through the artery, by means of a microwave sensor, to produce a continuous reading of the heart-rate. The measurement is insensitive to rhythmic relative movement of the sensor and subject, making it suitable for performing accurate heart-rate measurements, while the user is in training.

In a preferred embodiment, the measurement is performed on a human wrist, where the artery diameter varies by approximately 10% of its nominal value of approximately 2.5 mm during the pulse cycle.

The heart-rate sensor is located on a relevant body part, for example a limb above the artery to be measured. The proposed sensor transmits a microwave signal into the artery. The amplitude of the signal reflected from this artery depends on its instantaneous diameter, which in turn, represents the instantaneous blood pressure. Monitoring the rhythm or frequency of this reflection allows estimating the subject's heart-rate.

Three interference mechanisms exist in this measurement setup:

1. Additive interference: the sensor also receives reflected waves from other tissues. For example, the reflection from the subject's skin can be much stronger than the reflection from the artery. If the skin's reflection varies rhythmically, for example when the subject is jogging, it will interfere with the reflection from the artery, and reduce the measurement accuracy.
2. Multiplicative interference: The reflected signal that is received also depends on its distance from the target. As this distance varies rhythmically, the reflected signal from the artery will vary too. This will produce a spurious modulation on the reflected signal. This will introduce an unwanted interference to the measurement, as well.
3. The subject's artery diameter varies in relation to the body part acceleration, for example while running. This also changes the artery diameter, regardless the heart pulse.

As the rhythm, or frequency, of movement that cases the interferences can be in the same frequency range as the heart-rate to be measured, these interferences must be excluded from the measurement.

In order to separate between the required signal and the interferences, the present invention uses RADAR technology, namely FMCW, also sometimes called Linear FM (LFM) or chirp. This RADAR technology allows separating the reflections that originate from different distances from the antenna, thus allowing the separation of the reflection from different tissues. These different signals, one which originates primarily from the artery, and the others which originate from other tissue which are not responsive to the heart pulse, will allow separating the heart rate pulse signal, from interferences caused by the movement.

Figure 1:
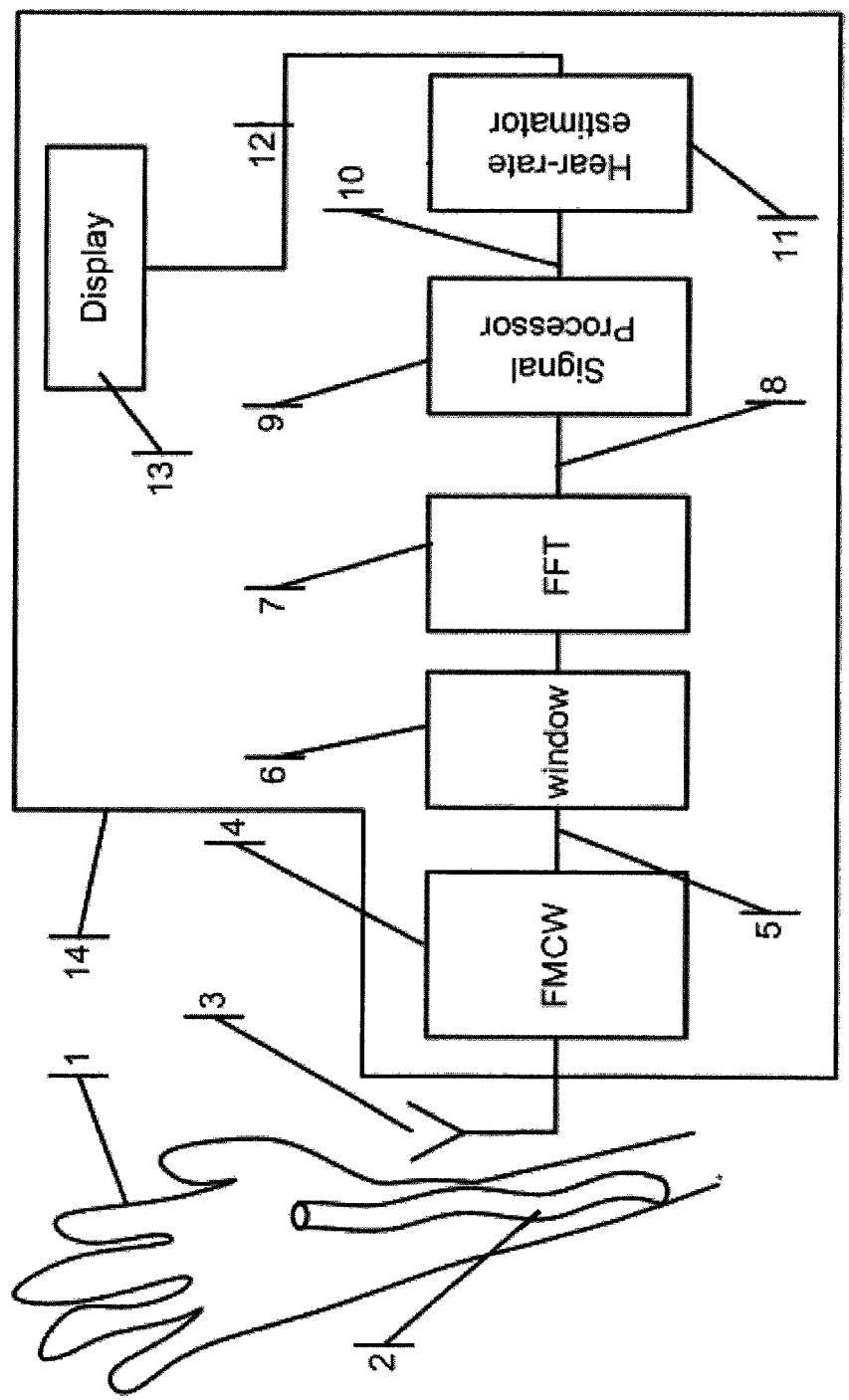
FIG. 1 is a top level block diagram usable in an embodiment of the invention.

The following discussion relates to pulse measurement from an artery that is embedded in a limb. The measured artery can also be embedded in other body parts, of humans or animals, and operate in the same manner. FIG. 1 shows a simplified block diagram of the sensor proposed by the present invention. The Sensor 14 is connected to antenna 3 for sensing the instantaneous volume of blood in the artery 2 to be measured. A Frequency Modulated Continuous Wave (FMCW) RADAR 4 transmits microwave signals into the subject limb 1, in this case into the arm, via antenna 3. The limb represents to the RADAR a multiplicity of tissue targets, each of which at a different distance from the antenna 3. The RADAR output 5 includes a superposition of signals, each of which corresponding to a specific tissue target. The frequency of each such a signal is related to the distance of the target, and its amplitude is related to the target's reflection strength, usually referred to as Radar Cross Section (RCS). An FFT function processor 7, followed by window function circuitry 6, splits the superposition of target information in output 5 according to its relative frequency, hence its distance, into a multiplicity of bins (bars that contain energy from a frequency range). Each bin output amplitude represents the RCS of the target at a specific distance from the antenna, which is equivalent to a specific depth inside the limb. Window function 6 is needed to suppress spectral sidebands originating from the abrupt start and stop of signal 5 (i.e., from the subsequent processor operating on time truncated data), due to using the FMCW radar.

Figure 2:
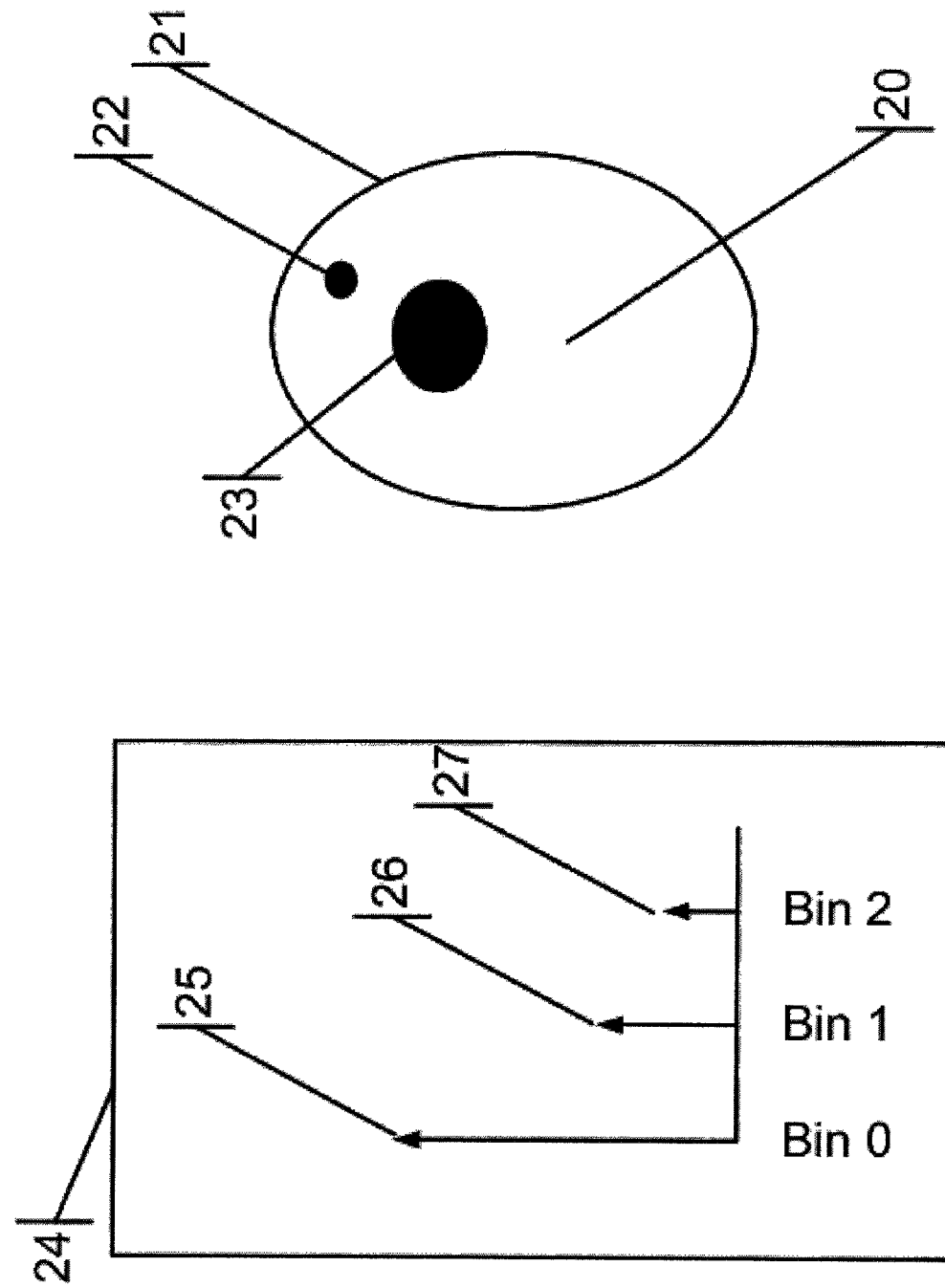
FIG. 2 is a cross section of a human arm, showing the location of the radial artery.

FIG. 2 shows an example of the FFT output in relation to the limb tissues. In this example, the limb is a human wrist. Its cross section 20 is shown, and includes for this simplistic illustration, three tissue elements: the skin 21, the artery 22, and a bone 23. The corresponding output of three FFT bins is shown in 24, and also correspond to output signal 5 in FIG. 1. Bin 0 signal is represented by vector 25. It is a result of the lowest frequency component of signal 5, and is related to the nearest tissue, the skin 21. Bin 1 signal is represented by vector 26, and is the result of the reflection from the farther situated artery 22. Bin 2 signal is represented by vector 27, and is the result of the reflection of the even farther situated bone 23. The different FFT bins are referred hereafter as range gates, as they represent signals originating from targets in different ranges.

Returning back to FIG. 1, the FFT bins are connected via bus 8 to signal processor 9. Signal processor's 9 task is to filter out the effect of the sensor movement in respect to the limb. Signal processor 9 generates a signal 10 that essentially represents only the reflection from the artery. Signal 10 amplitude is proportional to the artery dilatation, which varies in accordance with the blood pulsating in the artery and therefore, is an essentially periodic signal, whose frequency represents the heart-rate. Heart-rate Estimator 11 measures this frequency and forwards it for display 13 via signal 12.

In this example, the signal in bin 1 of the FFT represents the dilatation of the artery, and does not include the interfering signals from the other tissue elements, thus eliminating the additive interference described above. The signal in bin 1 does, however, include the multiplicative interference as described above. The signals in the other bins also include this same multiplicative interference, but do not include the time varying component associated with the heart-rate, as they are reflected from other tissue elements.

The sensor proposed by the present invention detects the multiplicative interference from the other bins, and uses it to cancel the interference on the bin representing the artery dilatation, namely bin 1 in this example. A simple implementation of this cancellation is achieved by dividing the amplitude of the signal resulting from the artery by the amplitude of a signal that does not originate from the artery.

Different tissues in a human wrist are located in tight proximity. For example, the distance of the artery from the skin and the artery's depth, is approximately 3.5 mm. In order to separate the signals reflected from so close objects, a large signal bandwidth is needed. For an FMCW application, the signal bandwidth should be at least 3 GHz, and optimal performance can be achieved with a bandwidth of 6 GHz or more.

According to a preferred embodiment of the invention, Ultra Wideband (UWB) spectral allocation between 3.1 GHz to 10.6 GHz is used, since it complies with the existing legislation permitting this use.

By using this frequency range for measuring tissues inside a limb, a range resolution of approximately 3 mm can be obtained. In a preferred embodiment of this invention, the FMCW sweep time is 10 μsec and the sampling frequency of the Analog to Digital Converter (ADC) is set to 3.2 MHz. With these parameters, the FFT will have 32 bins, with no zero padding (appending one or more zeros to the end of a signal). The FFT bin 0 will represent the reflection from the skin, and the bin 1 will predominantly represent the reflection from the artery.

In this preferred setup, the error free signal representing the reflection from the artery can be generated by calculating the weighted ratio of two polynomials, so that the error free resulting signal is calculated by:

$$Sig = \frac{b_0 + \Sigma(p_i(x_i))}{a_0 + \Sigma(q_i(x_i))}$$

where $p_i$ and $q_i$ are polynomials of arbitrary degree and $x_i$ are the signal amplitudes corresponding to the various FFT bins.

The index i represents the bin number, where i=0 represents bin 0. This calculation is repeated in relation to the FMCW chirp repetition.

The $p_i$ and $q_i$ coefficients can be fixed values, as in this preferred embodiment. In other embodiments they can be dynamically set by the processor 9 during a user initiated calibration phase, at start-up, or during the operation of the sensor. This way, different artery depths in different subjects can be handled. These weighting constants can also be adapted to handle the changing dielectric parameters of the subject, caused by physiological changes while exercising or by other reasons. Such physiological changes may be, for example, temperature changes of the tissue, changes in the sweat level on the skin surface, or changing in blood flow.

In an alternative embodiment, the interference associated with the relative movement, as well as the artifact interference can be eliminated using Multiple Reference ANC (Adaptive Noise Cancellation), as described in the thesis of "Multiple Reference Active Noise Control" by Yifeng Tu, Virginia Polytechnic Institute and State University March, 1997, the content of which is incorporated herein by reference. The inputs to this noise cancellation algorithm are a multiplicity of FFT bins, and possibly also inputs from an accelerometer or acceleration sensitive device, sensing the acceleration along one or more axes.

The adaptive algorithm may include Recursive Least Squares (RLS), least mean square (LMS) and their derivatives, such as Filtered-X LMS (FxLMS) or FuLMS.

Another possible implementation of this RADAR unit can be the pulsed RADAR method. Additionally, other frequency bands may be used. It should be recognized by those skilled in the art that the bandwidth needed for other RADAR types, for example pulsed RADAR, is at least the same bandwidth needed for the FMCW RADAR.

Other embodiments of this invention may include using other types of FMCW RADARs, for example Stepped Frequency Radar (SFR-a radar in which the echoes of stepped frequency pulses are synthesized in the frequency domain to obtain wider signal bandwidth, to achieve high range resolution, without increasing system complexity), triangle wave modulation, multirate ramp, and triangular wave modulation. Also, it is possible to use wide band sine wave modulation.

Figure 3:
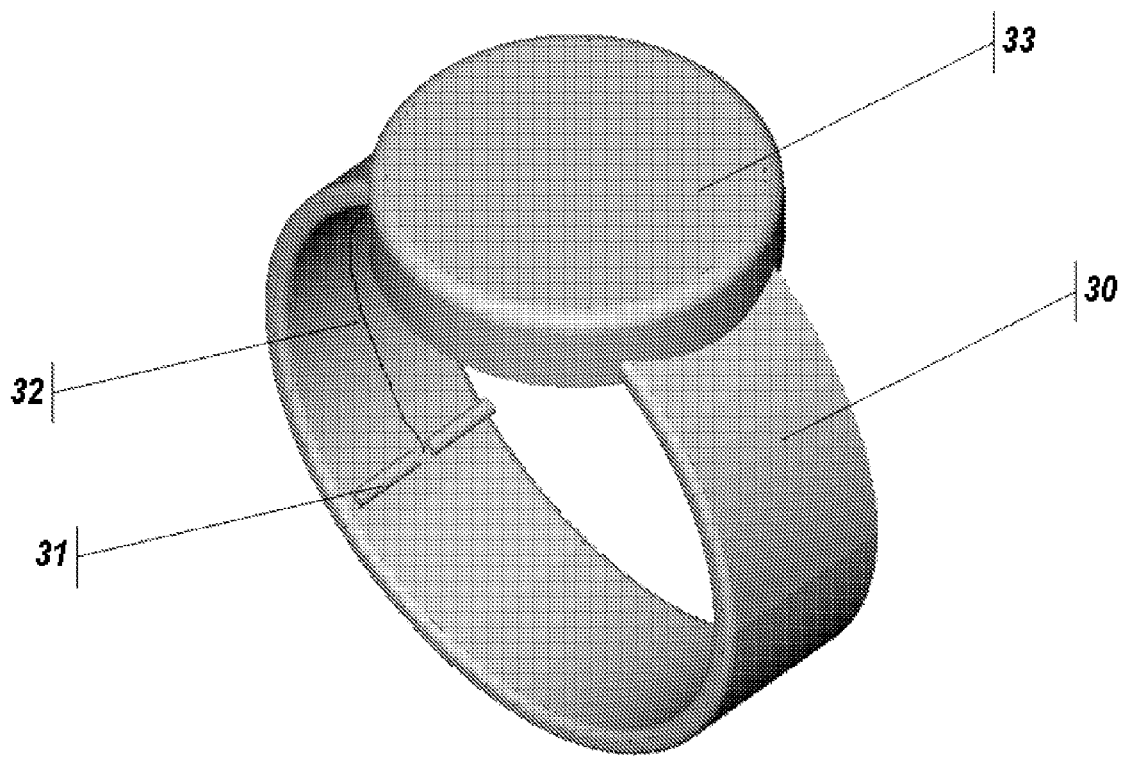
FIG. 3 is a simplified block diagram of the sensor integrated into a wristwatch, usable in an embodiment of the invention.

In a preferred embodiment of this invention, the sensor is integrated into a wristwatch, as shown in FIG. 3. The functional part of the proposed sensor 14 is mounted inside the wristwatch housing 33, and the antenna 31 is mounted in the wristwatch strap 30, above the radial artery. The antenna 31 is connected to the FMCW circuit via transmission line 32.

Figure 4:
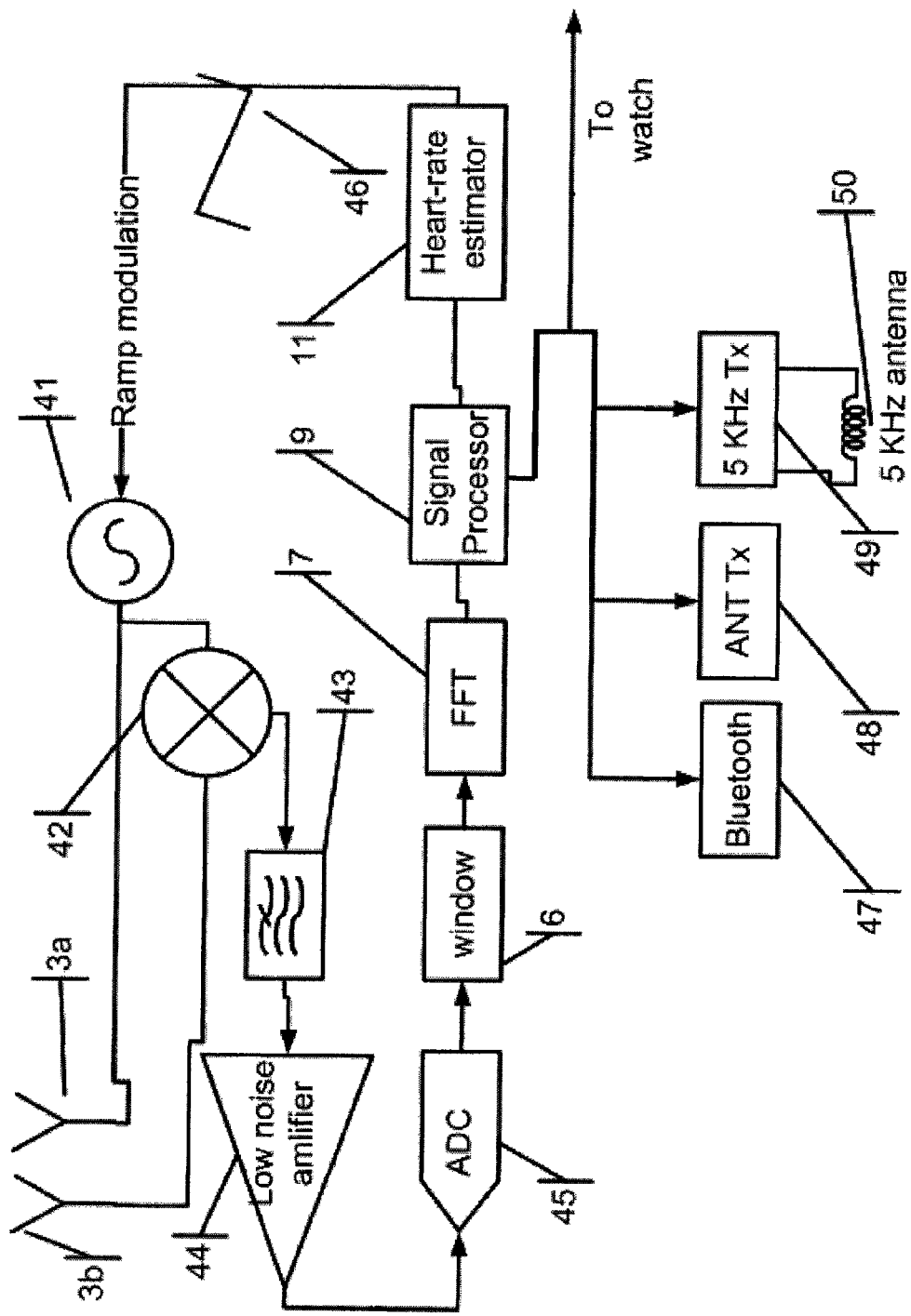
FIG. 4 is a block diagram of the sensor, usable in an embodiment of the invention.

FIG. 4 is a detailed block diagram of the sensor 14 to be embedded in the watch, according to a preferred embodiment of this invention. A voltage controlled oscillator (VCO) 41 (for generating the microwave signal) is modulated by a ramp signal 46 and spans the full signal bandwidth, which preferably spans from 3.1 to 10.6 GHz. A typical sweep time would be 10 μs. The selection of this sweep time will cause the detected signal representing the artery to be at approximately 125 KHz. This frequency is high enough to minimize the effect of the semiconductor's shot noise on the Signal to Noise Ratio (SNR). Other sweep times can be selected as needed in different practical implementations. In the preferred embodiment, the VCO output is coupled to the antenna 3a, and also to the LO input of mixer 42. In the preferred embodiment, the antenna 3b receives the reflected signal from the artery, that mixes with the VCO signal in Mixer 42, to produce an IF signal. This IF signal is filtered by a Low Pass Filter (LPF) 43 and amplified in IF amplifier 44, before being sampled by the Analog to Digital converter (ADC) 45. The IF channel illustrated in FIG. 4 describes a real signal detection.

Figure 5:
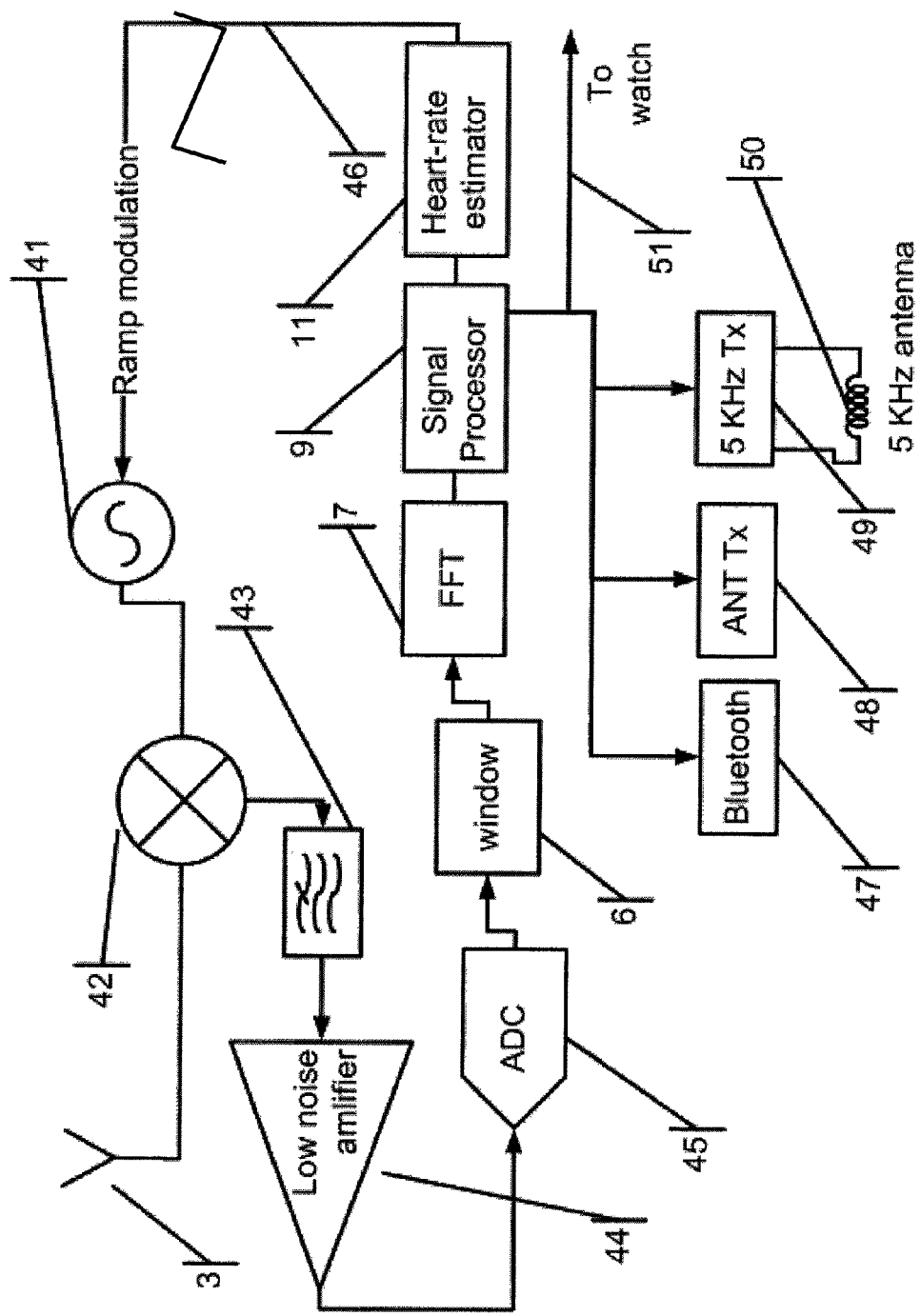
FIG. 5 is a block diagram of an alternative embodiment using a single antenna.

In an alternative embodiment, the dual antenna 3a and 3b is replaced with a single antenna 3, shown in FIG. 5. This antenna 3 is excited using its RF-to-LO parasitic leakage. The mixer may be purposely designed to leak this signal, which under other circumstances would be unwanted. Alternatively, other coupling mechanisms can be used, including a circulator or a directional coupler.

In both embodiments, the electrical length difference between signal transversing the antenna(s) via the skin reflection and the signal arriving a mixer LO port will define the IF frequency that corresponds to bin 0, or skin reflection. Making this electrical length sufficiently long allows using a single mixer. However, in some cases, specifically for a short electrical length difference, complex detection may be needed. Complex detection may be realized by using a quadrature mixer, and a pair each of LPFs, IF amplifiers, and ADCs. For a complex detection, the VCO needs to provide two outputs, with a constant phase difference of 90 degrees between them, which must be frequency independent in the sweep frequency range.

The requirement for a large frequency sweep range, and the requirement for a quadrature output, as well as the wish to integrate the microwave circuits and the signal processing circuits into a semiconductor die, can be met by realizing the VCO 41 as a variable frequency ring oscillator, such as a voltage controlled ring oscillator. Such a quadrature ring oscillator can be fabricated using standard CMOS or BiCMOS technologies.

Figure 7:
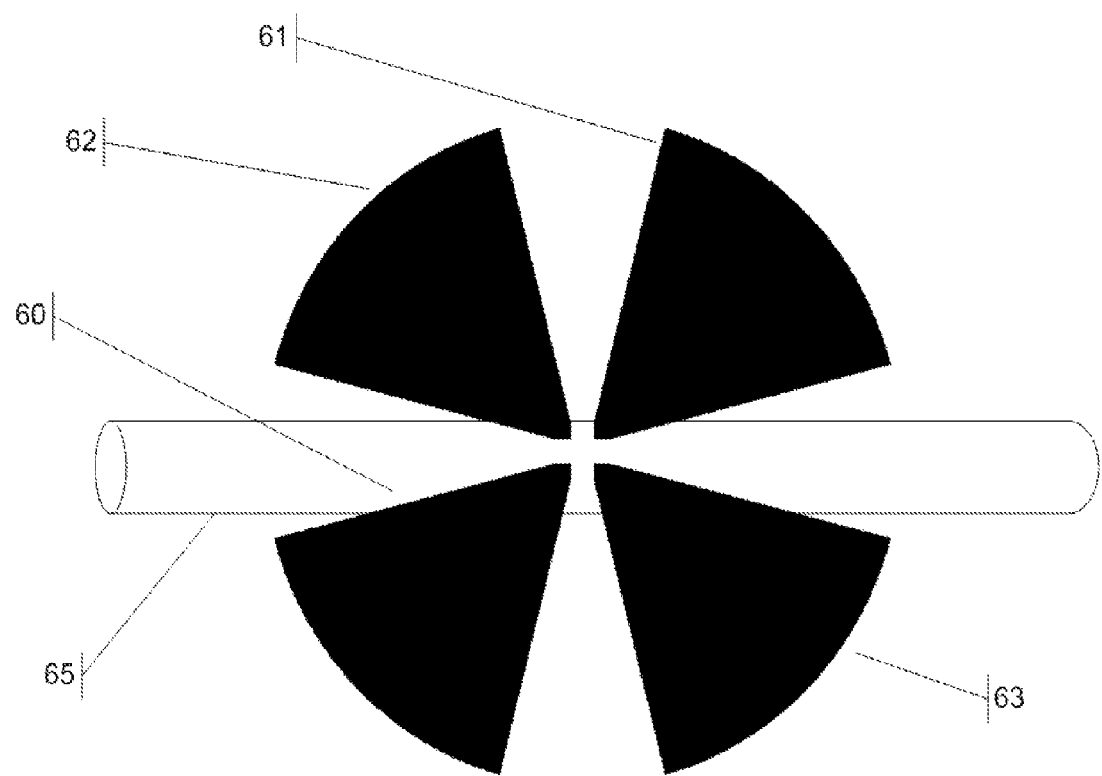
FIG. 7 shows a dual planar cross bow dipole antenna, used by the present invention.

In another preferred embodiment, the frequency variation of the oscillator may be in discrete steps, as in SFR, so digital control of the frequency is possible. The antennas 3a and 3b must support the broadband signal being used, while minimizing cross-talk between them. In this preferred embodiment, a dual planar cross-bow dipole antenna is used, as shown in FIG. 7. This antenna comprises two orthogonal broadband dipoles, one including conductors 60 and 61, and the other including conductors 62 and 63. Artery 65 is located in the X direction, to create an imbalance in the electromagnetic structure and thereby, contributing to the coupling between these dipoles. This allows the diameter or RCS of artery 65 to generate the received signal in the antenna.

An alternative embodiment includes a single antenna 3, as illustrated in FIG. 5. This antenna may be a single arm spiral antenna, a single broadband dipole antenna or a slot antenna. In this case, the reflected signal from the antenna is the received signal.

In the preferred embodiment, FFT 7 performs frequency analysis. Alternative embodiments can use other spectral analysis methods, for example: a DFT, a chirp-Z transform, or an analog filter bank. In the preferred embodiment, a window function 6 is a Kaiser window with β=0.5. Other window functions can be used, for example a Tukey Window (tapered cosine) or windows used in connection with Digital Fourier Transforms.

In an alternative embodiment, the heart-rate can be estimated using a correlation with a set of predefined wave shapes, each having a slightly different repetition rate. The candidate predefined wave with the highest correlation maximum will be selected as the best estimate. The highest maximum correlation may be detected by using a nonlinear estimator, such as a Maximum Likelihood Sequence Estimator (MLSE).

Figure 6:
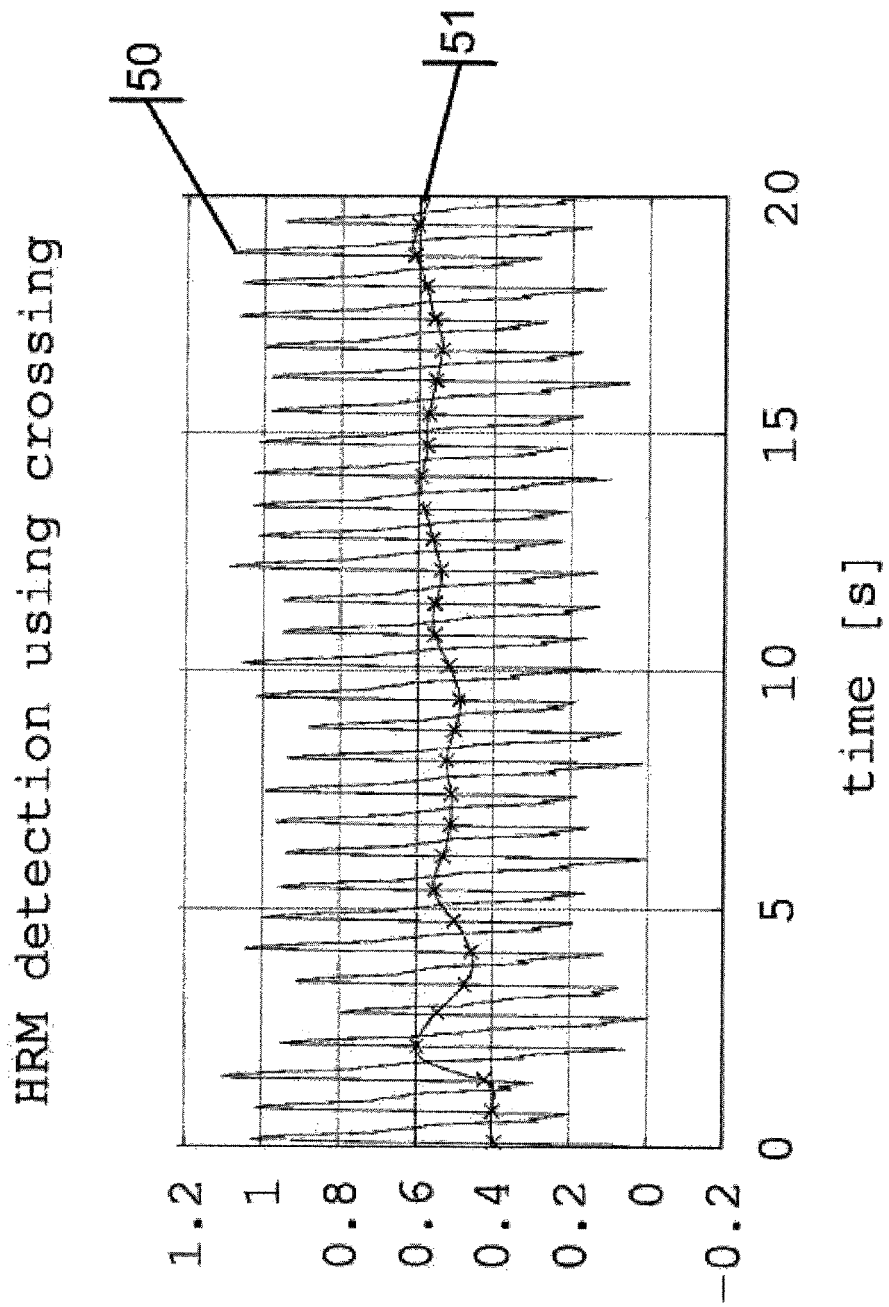
FIG. 6 shows the waveform of the detected pulse signal, and the points of extraction of heart-rate related measurements.

The signal Sig. 10 resulting from the weighted division shown in FIG. 4, is of the shape 50 of FIG. 6. This signal is processed by heart-rate estimator 11 of FIG. 4, to produce the estimated heart-rate frequency. The preferred detection method is to compare the signal Sig. of shape 50 to its running average 51, and counting the time interval Ti between subsequent positive direction zero crossings, as marked by asterisks on curve 51. In the preferred embodiment the running average is performed by a fourth order Butterworth filer having a 3 dB bandwidth of 0.5 Hz. The actual heart-rate is calculated by performing a running average on 6 measurements of 60/Ti, where Ti is in seconds. It is possible to use other spectral estimation methods to calculate the heart-rate, for example a Fourier transform.

Since the subject heart-rate cannot exceed a few Hertz, the preferred embodiment uses a sampling rate of 10 Hz. The RADAR subsystem needs to active at a duty cycle of 0.01%. This enables the sensor to consume a very low average power, and makes it suitable for coin battery operation. In alternative embodiments, a higher duty cycle can be used to produce a better signal to noise ratio, and to improve the reading accuracy. In this case, multiple measurements can be performed, and the results can be averaged to improve fidelity.

In a preferred embodiment, the heart-rate sensor is powered by a CR2032 3V lithium coin battery. It is also possible to aid the powering of the heart-rate sensor with other energy sources, for example a rechargeable battery, a solar cell, or an electric generator that generates electricity from the movement of the subject's hand. Any of these methods of generating and storing electrical energy can be combined.

In another embodiment, the heart-rate data can be transmitted to an external recipient that can display the results, such as exercise equipment (e.g., bicycles, exercise treadmills, rowing machines), smart phones, and others.

In another embodiment, the sensor may be used to sense the health of a subject, for example a senior person. In this case, the sensor will test the measured heart rate and will compare it to predefined limits or predefined heart rate variation pattern or heart rate variability. If the measurement exceeds predefined limits, it would then communicate this condition via a wireless communication channel, in order, for example, to alert medical care staff.

Many standards for this transmission exist, and a multiplicity of these communication protocols could be supported:

1. The 5 KHz coded protocol 49, which includes a 5 Khz signal that is PPM modulated by a pulse triplet, each with a width of 5-7 msec for each heart beat.
2. The 5 Khz uncoded protocol 50, which includes a 5 Khz signal that is PPM modulated by a single pulse with a width of approximately 25 msec for each heart beat.
3. The ANT standard 48.
4. The Bluetooth standard 47.

The sensor proposed by the present invention also facilitates heart rate measurements from a body part which is covered by an apparel (e.g., cloth, leather etc.) or by natural fur. For example, the sensor may be integrated into a shoe and is capable of measuring the heart rate of an animal through its fur.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A wearable sensor for detecting a signal corresponding to an artery's diameter, comprising:
    a first antenna configured for transmitting frequency modulated microwave signals whose frequencies span an ultra wideband into a body part containing the artery;
    a frequency modulated oscillator;
    a mixer configured to mix signals generated by said oscillator that are coupled to an input of said mixer from an output of said oscillator and reflected signals received by said first antenna or a second antenna that contain reflections of said frequency modulated microwave signals by tissue in said body part, and to output the mixed signals;
    an analogue to digital converter configured to sample said mixed signals and to output sampled data;
    a transform for receiving said sampled data and transforming said output data from frequency domain to time domain, and splitting the sampled data into a plurality of bins, wherein each bin stores bin data that corresponds to a amplitude of reflected signal from tissue located at a unique depth in the body part;
    a signal processor configured to receive said bin data from said function processor, and to use said bin data to generate a signal corresponding to the artery's diameter, and
    a battery for powering the sensor.

2. The wearable sensor of claim 1, further comprising a window function circuitry configured for suppressing unwanted spectral sidebands resulting from a transmitting said frequency modulated microwave signals as pulses.

3. The wearable sensor according to claim 2, wherein the window function comprises at least one of a Kaiser window, a Tukey window and a window used in connection with Digital Fourier Transforms.

4. The wearable sensor of claim 1, further comprising a heart-rate estimator configured for estimating a heart-rate by at least measuring the frequency of the artery dilatation variations.

5. The wearable sensor of claim 4, wherein the heart-rate estimator is additionally configured to cancel interference of the amplitude of a signal not originating from the artery.

6. The wearable sensor of claim 5, wherein the interference is eliminated via at least one of Multiple Reference Active Noise Control, Recursive Least Squares (RLS), Least Mean Square (LMS), Filtered-X Least Mean Square, and Filtered-u Least Mean Square.

7. The wearable sensor of claim 5, wherein the interference cancellation corresponds to an adaptive noise cancellation having input signals comprising a plurality of range gate bins amplitudes.

8. The wearable sensor of claim 5, wherein the interference cancellation corresponds to adaptive noise cancellation, wherein one or more additional inputs are received from an acceleration sensitive device.

9. The wearable sensor of claim 1, further comprising a radio transmitter configured to relay heart rate data to a remote receiver or terminal.

10. The wearable sensor of claim 1, wherein the interference cancellation corresponds to a ratio of polynomials of multiplicity of range gate bins amplitudes.

11. The wearable sensor of claim 10, wherein the ratio comprises the ratio between the amplitude of the reflected signal from the artery to the amplitude of the reflected signal from the skin.

12. The wearable sensor of claim 1, further comprising a blood-flow volume per unit estimator using data comprising said signal corresponding to diameter of the artery to estimate blood-flow volume.

13. The wearable sensor of claim 1, wherein the frequency modulated microwave signals transmitted into the tissue comprise frequency-modulated continuous wave signals with a duty cycle of less than 1%.

14. The wearable sensor of claim 13, wherein the frequency-modulated continuous wave signals are modulated by a triangular wave, a multi-rate ramp, or a wideband sine-wave signal.

15. The wearable sensor of claim 13, wherein the frequency-modulated continuous wave signals are chirp pulses having a frequency width of at least 5 GHz.

16. The wearable sensor of claim 13, wherein the frequency-modulated continuous wave signal comprise a sweep time of 10 μsec and the analogue to digital converter includes a sampling frequency of 3.2 MHZ.

17. The wearable sensor of claim 1, wherein the function processor is configured for splitting the sampled data into a plurality of bins using a Fast Fourier Transform.

18. The wearable sensor of claim 1, wherein the frequency modulated microwave signals transmitted into the tissue comprise stepped-frequency signals with a duty cycle of less than 1%.

19. The wearable sensor of claim 1, wherein the sensor is integrated with a wrist watch, or further comprising a wrist strap enabling the sensor to be worn on the wrist.

20. The wearable sensor of claim 1, wherein the oscillator is a voltage controlled oscillator and the voltage controlled oscillator is modulated by a ramp signal spanning a signal bandwidth between 3.1 to 10.6 GHz with a sweep time of 10 μsec.

21. The wearable sensor according to claim 1, wherein the oscillator is a voltage controlled oscillator and the voltage controlled oscillator is a variable frequency ring oscillator, fabricated from CMOS or BicMOS technologies.

22. The wearable sensor of claim 1, wherein the frequency variations of the oscillator are performed in discrete steps.

23. The wearable sensor of claim 1, wherein the antenna comprises a dual planar cross-bow dipole antenna including two orthogonal broadband dipoles, a single arm spiral antenna, a single broadband dipole antenna, or a slot antenna.

24. The wearable sensor of claim 1, wherein the function processor is configured to use a discrete Fourier transform, a chirp-z transform, or an analog filter bank.

25. The wearable sensor of claim 1, wherein the signal is sampled at 10 Hz.

26. The wearable sensor of claim 1, further comprising cancellation circuitry configured for cancellation of interference caused by the sensor movements utilizing signals from a plurality of time bins.

27. The wearable sensor of claim 1, wherein the oscillator is a voltage controlled oscillator and the voltage controlled oscillator is a variable frequency ring oscillator.

28. The wearable sensor of claim 1, wherein the oscillator's bandwidth is more than 5 GHz.

29. The wearable sensor of claim 1, wherein the oscillator is a voltage controlled oscillator.

30. The wearable sensor of claim 1 wherein said reflected signals are received by said first antenna.

31. The wearable sensor of claim 1 wherein said first antenna and said first or second antenna are a single antenna for performing both transmit and receive.

32. The wearable sensor of claim 31 wherein an output of said oscillator is coupled to said mixer and said mixer is a leaky mixer which leaks some of the signal it receives from the oscillator to said single antenna.

33. The wearable sensor of claim 1 wherein said mixer outputs an IF signal having an IF center frequency centered at a difference in frequency, of the frequency of the oscillator signal received at the mixer, and the frequency of the reflected signal received at the mixer, and wherein said IF center frequency corresponds to the signal transmission time from the mixer to the artery and from the artery to the mixer times the change in signal frequency over that signal transmission time.

34. The wearable sensor of claim 33 wherein the signal transmission time from the mixer to the artery and from the artery to the mixer includes the time for the signal to traverse approximately 7 mm within the body.

35. The wearable sensor of claim 33, wherein said signal frequency is modulated over at least 3 GHz in 10 μsec.

36. The wearable sensor of claim 1, wherein said frequency signal is modulated at a frequency ramp rate of between 3 and 7.5 times $10^5$ Ghz/second.

37. The wearable sensor of claim 1, wherein said frequency modulated oscillator comprises a voltage controlled oscillator modulated by a modulation signal causing the oscillator to oscillate over bandwidth of at least 3 GHz.

38. The wearable sensor of claim 1, wherein:
said signal processor comprises noise cancellation for removing multiplicative interference due to variation in distance between the artery and the antenna or antennas transmitting and receiving the frequency modulated microwave signals, by determining multiplicative interference from bin data for reflections from tissue other than the artery, and removing the determined multiplicative interference from the additive interference-free artery data.

39. The wearable sensor of claim 1, wherein:
said signal processor comprises noise cancellation for removing additive interference due to bin data corresponding to reflection from tissue other than the artery, to thereby produce additive interference-reduced artery data corresponding substantially to reflections from the artery without additive interference.

40. The wearable sensor of claim 1, wherein said mixer is designed to leak signal received from the frequency modulated oscillator to said first antenna and to receive said reflected signals from said first antenna.

41. The wearable sensor of claim 1, where said frequency modulated oscillator received an input signal that provides one of a ramp and a stepped control signal to control the frequency modulated oscillator to generate one of a chirped and stepped signal for which the chirp or steps span a bandwidth of at least 3 Ghz.

42. The wearable sensor of claim 1 wherein said mixer is configured to mix reflected signals that are reflected from an artery at a depth of 3.5 mm below the skin.

43. The wearable sensor of claim 1 wherein said signal processor is configured to generate said signal corresponding to the artery's diameter based upon reflections from an artery having a nominal diameter of 2.5 mm.

44. The wearable sensor of claim 1 wherein said a signal processor is configured to generate the signal corresponding to the artery's diameter at a rate above a few Hertz.

45. The wearable sensor of claim 1 wherein said frequency modulated oscillator is configured to operate at a duty cycle between 0.01% and 1%.

46. A wearable sensor for detecting time varying dilation diameter of an artery in a subject, comprising:
a frequency modulated oscillator;
a first antenna for transmitting frequency modulated microwave signals whose frequencies span an ultra-wideband into a body part of the subject, said body part including the artery;
a second antenna for sensing reflections of signals transmitted by said first antenna by said body part;
a mixer configured to mix a signal generated by said oscillator that is coupled to an input of said mixer from an output of said oscillator and a signal received from the second antenna;
an analogue to digital converter configured to sample a signal generated by the mixer;
a transform following said analogue to digital converter and configured for splitting the sampled data into a plurality of bins, wherein each bin corresponds to a target located at a unique depth in the tissue and represents a amplitude of said reflected signal on said target;
a signal processor configured for generating a signal corresponding to the diameter of the artery; and
a battery for powering the sensor.

47. The wearable sensor of claim 46 wherein said signal processor is further configured for filtering out the (1) signal corresponding to tissue other than the artery and (2) the effect of the sensor movement with respect to the body part.

48. A method for measuring the heart-rate in a subject, comprising:
transmitting frequency modulated microwave signals whose frequencies span an ultra wideband, via a wearable unit into a subject's body part, the body part including an artery;
receiving reflected signals in an antenna; wherein the amplitudes of the reflected signals relate to the target's reflection strength;
converting said reflected signals to digital representation;
suppressing spectral sidebands;
splitting said superposition by using a transform function according to its relative frequency into a multiplicity of bins, each of which having an amplitude that represents the reflection magnitude of a target at a specific distance from said antenna;
using the bin data to generate an artery dilation signal having an amplitude representative of the varying artery dilatation due to heart-rate;
measuring the frequency of the artery dilation variations; and
determining the heart rate based on the measured frequency.

49. The method of claim 48 further comprising the step of filtering out the affect of acceleration using an acceleration signal, on artery dilation, prior to measuring frequency of artery dilation.

50. The method of claim 48, wherein said transmitting of the frequency modulated microwave signals via the wearable unit into the subject's body part comprises coupling an output of a frequency modulated oscillator to an input of a mixer, and coupling an output of the mixer to said antenna.

51. The method of claim 50, wherein said converting the reflected signals to digital representation comprises coupling signals received by said antenna to an input of said mixer so that said mixer mixes the output of the frequency modulated oscillator with the signals received by said antenna.

52. The method of claim 51 wherein said mixer is designed to leak signal received from the frequency modulated oscillator to the antenna.

53. The method of claim 48 further comprising generating said frequency modulated microwave signals using a frequency modulated oscillator whose output frequency is controlled by an input in the form of a ramped or stepped signal.

54. The method of claim 48 further comprising filtering out the bin data the effect of the sensor movement with respect to the subject body part and the effect of signals from tissue other than the artery.

* * * * *